(12) United States Patent
Thacker et al.

(10) Patent No.: US 9,295,840 B1
(45) Date of Patent: Mar. 29, 2016

(54) SYSTEMS AND METHODS FOR AUTOMATICALLY PROGRAMMING PATIENT THERAPY DEVICES

(71) Applicant: Nevro Corporation, Menlo Park, CA (US)

(72) Inventors: James R. Thacker, Homer, AK (US); Jon Parker, San Jose, CA (US)

(73) Assignee: Nevro Corporation, Redwood City, CA (US)

( * ) Notice: Subject to any disclaimer, the term of this patent is extended or adjusted under 35 U.S.C. 154(b) by 0 days.

(21) Appl. No.: 14/161,554

(22) Filed: Jan. 22, 2014

Related U.S. Application Data

(60) Provisional application No. 61/755,393, filed on Jan. 22, 2013.

(51) Int. Cl.
*A61N 1/372* (2006.01)
*A61N 1/36* (2006.01)

(52) U.S. Cl.
CPC .................................. *A61N 1/36071* (2013.01)

(58) Field of Classification Search
CPC .............. A61N 1/0551; A61N 1/3605; A61N 1/36139; A61N 1/36142
USPC .......................................................... 607/46
See application file for complete search history.

(56) References Cited

U.S. PATENT DOCUMENTS

| | | | |
|---|---|---|---|
| 4,210,151 A | 7/1980 | Keller, Jr. | |
| 4,257,429 A * | 3/1981 | Dickhudt et al. | 607/116 |
| 4,340,063 A | 7/1982 | Maurer | |
| 5,016,635 A | 5/1991 | Graupe | |
| 5,063,929 A | 11/1991 | Bartelt et al. | |
| 5,159,926 A | 11/1992 | Ljungstroem | |
| 5,184,617 A | 2/1993 | Harris et al. | |

(Continued)

FOREIGN PATENT DOCUMENTS

| | | |
|---|---|---|
| JP | 08503648 | 4/1996 |
| JP | 20020527159 | 8/2002 |

(Continued)

OTHER PUBLICATIONS

Keuchmann C et al., "853 Could Automatic Position Adaptive Stimulation be Useful in Spinal Cord Stimulation," Abstract, Medtronic, Inc., undated, 1 page.

(Continued)

*Primary Examiner* — Alyssa M Alter
(74) *Attorney, Agent, or Firm* — Perkins Coie LLP

(57) ABSTRACT

Methods for automatically programming a signal generator in a patient therapy system and associated systems are disclosed. A representative method comprises retrieving data including therapy program parameters, level of efficacy, and medication use corresponding to a plurality of time periods; identifying from the data a target time period having a corresponding level of efficacy; determining from the data if medication was used during the target time period; determining from the data if medication was used during a prior time period immediately before the target time period; calculating a lead position confidence factor; and programming the signal generator to repeat therapy with the therapy program parameters corresponding to the target time period if the confidence factor is greater than a threshold value and medication was used during the prior time period and not during the target time period.

11 Claims, 6 Drawing Sheets

(56) References Cited

U.S. PATENT DOCUMENTS

| | | |
|---|---|---|
| 5,222,494 A | 6/1993 | Baker, Jr. |
| 5,540,730 A | 7/1996 | Terry, Jr. et al. |
| 5,641,326 A | 6/1997 | Adams |
| 5,702,429 A | 12/1997 | King |
| 5,782,884 A | 7/1998 | Stotts et al. |
| 5,891,179 A | 4/1999 | Er et al. |
| 5,913,882 A | 6/1999 | King |
| 5,938,690 A | 8/1999 | Law |
| 6,155,267 A | 12/2000 | Nelson |
| 6,308,102 B1 | 10/2001 | Sieracki et al. |
| 6,353,762 B1 | 3/2002 | Baudino et al. |
| 6,381,496 B1 | 4/2002 | Meadows et al. |
| 6,440,090 B1 | 8/2002 | Schallhorn |
| 6,516,227 B1 | 2/2003 | Meadows et al. |
| 6,574,507 B1 | 6/2003 | Bonnet |
| 6,587,727 B2 | 7/2003 | Osorio et al. |
| 6,609,030 B1 | 8/2003 | Rezai et al. |
| 6,622,048 B1 | 9/2003 | Mann |
| 6,803,102 B1 | 10/2004 | Talley et al. |
| 6,895,280 B2 | 5/2005 | Meadows et al. |
| 6,947,792 B2 | 9/2005 | Ben-Haim et al. |
| 6,978,171 B2 | 12/2005 | Goetz et al. |
| 6,993,384 B2 | 1/2006 | Bradley et al. |
| 7,020,523 B1 | 3/2006 | Lu et al. |
| 7,024,246 B2 | 4/2006 | Acosta et al. |
| 7,050,856 B2 | 5/2006 | Stypulkowski |
| 7,110,821 B1 | 9/2006 | Ross |
| 7,123,967 B2 | 10/2006 | Weinberg |
| 7,127,296 B2 | 10/2006 | Bradley |
| 7,174,215 B2 | 2/2007 | Bradley |
| 7,184,837 B2 | 2/2007 | Goetz |
| 7,206,632 B2 | 4/2007 | King |
| 7,239,920 B1 | 7/2007 | Thacker et al. |
| 7,239,926 B2 | 7/2007 | Goetz |
| 7,242,984 B2 | 7/2007 | DiLorenzo |
| 7,263,402 B2 | 8/2007 | Thacker et al. |
| 7,266,412 B2 | 9/2007 | Stypulkowski |
| 7,317,948 B1 | 1/2008 | King et al. |
| 7,343,200 B2 | 3/2008 | Litvak et al. |
| 7,444,181 B2 | 10/2008 | Shi et al. |
| 7,447,545 B2 | 11/2008 | Heruth et al. |
| 7,463,927 B1 | 12/2008 | Chaouat |
| 7,617,002 B2 | 11/2009 | Goetz |
| 7,747,330 B2 | 6/2010 | Nolan et al. |
| 7,819,909 B2 | 10/2010 | Goetz et al. |
| 7,831,307 B1 | 11/2010 | Moffitt |
| 7,853,322 B2 | 12/2010 | Bourget et al. |
| 7,872,884 B2 | 1/2011 | Parramon et al. |
| 7,945,330 B2 | 5/2011 | Gliner et al. |
| 7,957,797 B2 | 6/2011 | Bourget et al. |
| 7,957,809 B2 | 6/2011 | Bourget et al. |
| 7,957,814 B2 | 6/2011 | Goetz et al. |
| 8,016,776 B2 | 9/2011 | Bourget et al. |
| 8,116,878 B1 | 2/2012 | Palmer |
| 8,121,703 B1 | 2/2012 | Palmer |
| 8,170,675 B2 | 5/2012 | Alataris et al. |
| 8,311,639 B2 | 11/2012 | Parker et al. |
| 8,355,797 B2 | 1/2013 | Caparso et al. |
| 8,457,759 B2 | 6/2013 | Parker et al. |
| 8,498,710 B2 | 7/2013 | Walker et al. |
| 8,626,312 B2 | 1/2014 | King et al. |
| 8,676,331 B2 | 3/2014 | Parker |
| 8,712,533 B2 | 4/2014 | Alataris et al. |
| 8,712,535 B2 | 4/2014 | Walker et al. |
| 2002/0107553 A1 | 8/2002 | Hill et al. |
| 2003/0093134 A1 | 5/2003 | Bradley |
| 2003/0153959 A1 | 8/2003 | Thacker et al. |
| 2003/0195582 A1 | 10/2003 | Mann |
| 2004/0015202 A1 | 1/2004 | Chandler et al. |
| 2004/0167584 A1 | 8/2004 | Carroll et al. |
| 2005/0060001 A1 | 3/2005 | Singhal et al. |
| 2005/0060007 A1 | 3/2005 | Goetz |
| 2005/0245987 A1 | 11/2005 | Woods et al. |
| 2006/0161236 A1 | 7/2006 | King |
| 2006/0195159 A1 | 8/2006 | Bradley et al. |
| 2006/0247732 A1 | 11/2006 | Wesselink |
| 2006/0253174 A1 | 11/2006 | King |
| 2006/0253182 A1 | 11/2006 | King |
| 2006/0259099 A1 | 11/2006 | Goetz et al. |
| 2007/0150029 A1 | 6/2007 | Bourget et al. |
| 2007/0208394 A1 | 9/2007 | King et al. |
| 2007/0245318 A1 | 10/2007 | Goetz et al. |
| 2007/0249968 A1 | 10/2007 | Miesel et al. |
| 2007/0265679 A1 | 11/2007 | Bradley et al. |
| 2007/0276450 A1 | 11/2007 | Meadows et al. |
| 2008/0015657 A1 | 1/2008 | Haefner |
| 2008/0046036 A1* | 2/2008 | King et al. ............... 607/59 |
| 2008/0064980 A1 | 3/2008 | Lee et al. |
| 2008/0183256 A1 | 7/2008 | Keacher |
| 2008/0188909 A1 | 8/2008 | Bradley |
| 2008/0215118 A1 | 9/2008 | Goetz et al. |
| 2008/0234791 A1 | 9/2008 | Arle et al. |
| 2008/0281381 A1 | 11/2008 | Gerber et al. |
| 2009/0018617 A1 | 1/2009 | Skelton et al. |
| 2009/0112282 A1 | 4/2009 | Kast et al. |
| 2009/0125079 A1 | 5/2009 | Armstrong et al. |
| 2009/0204173 A1 | 8/2009 | Fang et al. |
| 2009/0281599 A1 | 11/2009 | Thacker et al. |
| 2009/0326608 A1 | 12/2009 | Huynh et al. |
| 2010/0010566 A1 | 1/2010 | Thacker et al. |
| 2010/0049280 A1 | 2/2010 | Goetz |
| 2010/0125314 A1 | 5/2010 | Bradley et al. |
| 2010/0131034 A1 | 5/2010 | Gliner et al. |
| 2010/0137944 A1 | 6/2010 | Zhu |
| 2010/0185256 A1 | 7/2010 | Hulvershorn |
| 2010/0211135 A1 | 8/2010 | Caparso et al. |
| 2010/0274312 A1 | 10/2010 | Alataris et al. |
| 2010/0274314 A1 | 10/2010 | Alataris et al. |
| 2010/0274317 A1 | 10/2010 | Parker et al. |
| 2010/0305631 A1 | 12/2010 | Bradley et al. |
| 2011/0009927 A1 | 1/2011 | Parker et al. |
| 2011/0029040 A1 | 2/2011 | Walker et al. |
| 2011/0040351 A1 | 2/2011 | Butson et al. |
| 2011/0093051 A1 | 4/2011 | Davis et al. |
| 2012/0083857 A1 | 4/2012 | Bradley et al. |
| 2012/0116476 A1 | 5/2012 | Kothandaraman |
| 2012/0130448 A1 | 5/2012 | Woods et al. |
| 2012/0172946 A1 | 7/2012 | Alataris et al. |
| 2012/0253422 A1 | 10/2012 | Thacker et al. |
| 2012/0265268 A1 | 10/2012 | Blum et al. |
| 2012/0265271 A1 | 10/2012 | Goetz |
| 2013/0023950 A1 | 1/2013 | Gauthier |
| 2013/0060302 A1 | 3/2013 | Polefko et al. |
| 2013/0066411 A1 | 3/2013 | Thacker et al. |
| 2013/0116754 A1 | 5/2013 | Sharma et al. |
| 2013/0261694 A1 | 10/2013 | Caparso et al. |
| 2013/0310892 A1 | 11/2013 | Parker et al. |
| 2014/0330338 A1 | 11/2014 | Walker et al. |
| 2015/0217113 A1 | 8/2015 | Walker et al. |

FOREIGN PATENT DOCUMENTS

| | | |
|---|---|---|
| JP | 2006502811 A | 1/2006 |
| JP | 2006212458 A | 8/2006 |
| JP | 2008526299 A | 7/2008 |
| JP | 2008534168 A | 8/2008 |
| JP | 2009519771 A | 5/2009 |
| WO | WO-2006119046 A1 | 11/2006 |
| WO | WO-2007149018 A1 | 12/2007 |
| WO | WO-2008142402 A1 | 11/2008 |

OTHER PUBLICATIONS

U.S. Appl. No. 14/161,152, filed Jan. 22, 2014, Thacker et al.
U.S. Appl. No. 14/161,592, filed Jan. 22, 2014, Thacker et al.
Hayt et al., "Engine Circuit Analysis," McGraw-Hill Book Company, Fourth Edition, 1986, 18 pages.

* cited by examiner

SYSTEMS AND METHODS FOR AUTOMATICALLY PROGRAMMING PATIENT THERAPY DEVICES

CROSS-REFERENCE TO RELATED APPLICATIONS

The present application claims the benefit of U.S. Provisional Application No. 61/755,393, filed Jan. 22, 2013, the disclosure of which is hereby incorporated by reference in its entirety. The present application is related to concurrently filed, co-pending applications, the disclosures of which are hereby incorporated by reference in their entireties. To the extent the forgoing materials and/or any other materials incorporated herein by reference conflict with the present disclosure, the present disclosure controls.

TECHNICAL FIELD

The present disclosure is directed generally to implantable neurological stimulation systems and methods. More specifically, the disclosure is directed to methods for automatically programming patient therapy systems, such as high frequency spinal cord stimulation systems that do not use paresthesia to mask or cover a patient's sensation of pain.

BACKGROUND

Neurological stimulators have been developed to treat pain, movement disorders, functional disorders, spasticity, cancer, cardiac disorders, and various other medical conditions. Implantable neurological stimulation systems generally have an implantable signal generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings (i.e. contacts) spaced apart from each other at the distal end of the lead body. The conductive rings operate as individual electrodes and, in many cases, the SCS leads are implanted percutaneously through a needle inserted into the epidural space, with or without the assistance of a stylet.

Once implanted, the signal generator applies electrical pulses to the electrodes, which in turn modify the function of the patient's nervous system, such as by altering the patient's responsiveness to sensory stimuli and/or altering the patient's motor-circuit output. In SCS for the treatment of pain, the signal generator applies electrical pulses to the spinal cord via the electrodes. In conventional SCS, "low frequency" electrical pulses are used to generate sensations (known as paresthesia) that mask or otherwise alter the patient's sensation of pain. For example, in many cases, patients report paresthesia as a tingling sensation that is perceived as less uncomfortable than the underlying pain sensation. Recently, a form of "high frequency" SCS has been developed, wherein high frequency electrical pulses are delivered to the spinal cord and are able to treat the patient's sensation of pain without generating paresthesia or otherwise using paresthesia to mask the patient's sensation of pain.

With conventional SCS, effective treatment has required clinicians with special skills and knowledge regarding spinal anatomy and the ability to manipulate stimulation induced paresthesia based on real time patient feedback (e.g., sensation of paresthesia). This results in an expensive and time consuming process. With the advent of high frequency SCS (e.g., frequencies of several thousand Hz), in some embodiments, the actual programming no longer requires such extensive knowledge of spinal anatomy or manipulation of stimulation induced paresthesia. However, it is still necessary for the clinician to process multiple pieces of information to determine the next programming steps. Even though high frequency SCS provides more effective therapy with less clinician involvement, there are still a very large number of possible combinations of electrode configurations and stimulation parameter combinations that can be considered in choosing a therapy program. In addition, the patient may undertake activities and/or other treatment regimens that add further variables, and therefore further complicate the process of identifying appropriate/optional active electrodes and/or other stimulation parameters. Thus, even with high frequency SCS, setting up and programming SCS systems presents a significant service burden on clinicians. Accordingly, there remains a need for improved systems to efficiently identify optimal treatment programs.

SUMMARY

Disclosed herein are methods and associated systems for automatically programming a signal generator in a patient therapy system, such as a spinal cord stimulation system. Automatically programming the signal generator can significantly reduce the burden on practitioners who administer SCS therapy to patients. In a representative embodiment, one such method comprises retrieving data for a first therapy program and selecting a second therapy program based on the retrieved data. The retrieved data can include therapy program parameters (e.g., active electrode location, signal amplitude, frequency and/or pulse width), data representative of a level of efficacy, and medication use corresponding to, related to, or otherwise directly functionally linked with a plurality of time periods (e.g., one day). The method can further include, identifying from the data, a target time period having a corresponding level of efficacy (e.g., a level below a threshold level); determining from the data if medication was used during the target time period; determining from the data if medication was used during a prior time period immediately before the target time period; calculating a lead position confidence factor; and programming the signal generator to repeat therapy with the therapy program parameters corresponding to the target time period if the confidence factor is greater than a threshold value and medication was used during the prior time period and not during the target time period. In one aspect of the present technology disclosed herein, the patient inputs the level of efficacy and the medication use into the signal generator via a patient remote. In some embodiments, the patient can also input an activity level. The level of efficacy may correspond to data representative of a level of pain relief, for example. A corresponding system may further comprise at least one memory unit housed in the signal generator or an external (e.g., remote) device to record the level of efficacy and the medication use.

DETAILED DESCRIPTION

Figure 1:
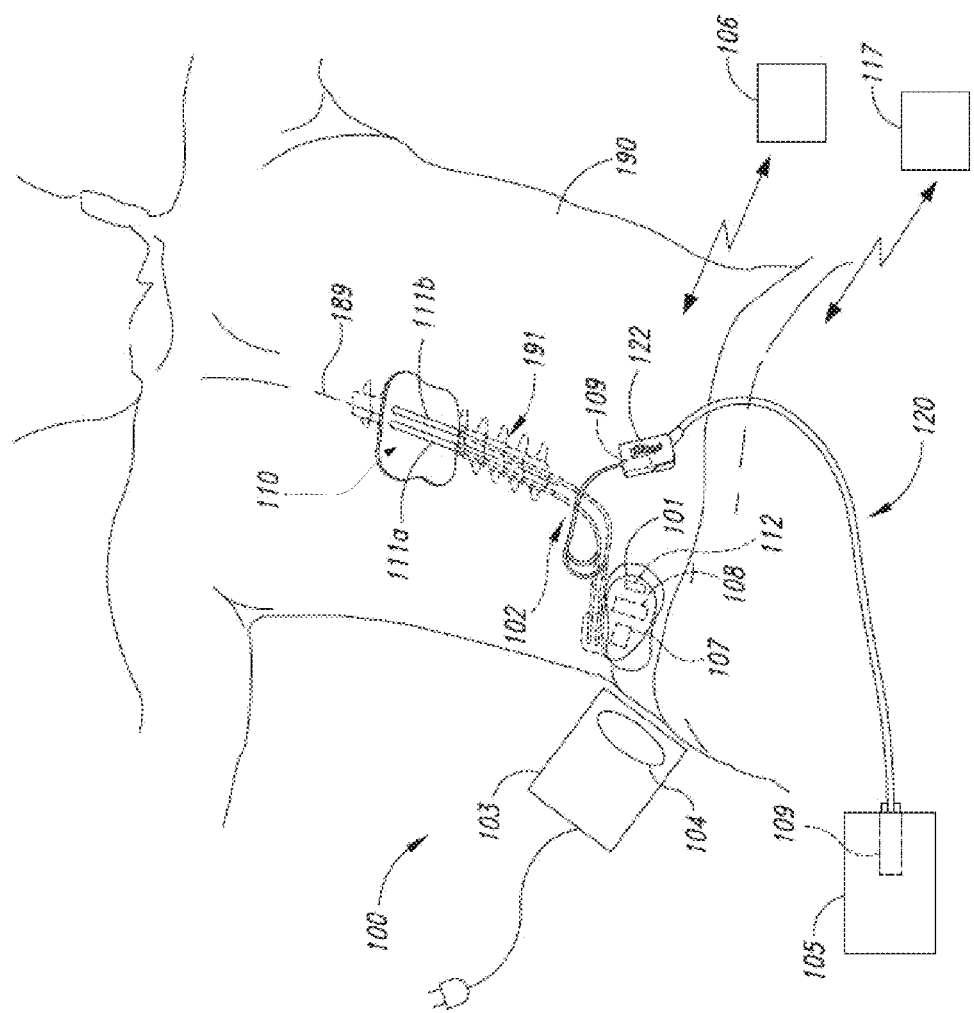
FIG. 1 is a partially schematic illustration of an implantable spinal cord stimulation system positioned at the spine to deliver therapeutic signals in accordance with several embodiments of the present technology.

The present technology is directed generally to methods for automating the process of finding an improved (e.g., most effective) set of parameters, or program, for patient therapy systems, such as spinal cord stimulation (SCS) systems. For example, in one embodiment, the present technology is employed in SCS systems that provide pain relief without generating paresthesia, such as "high frequency" SCS. Automating the process of finding the most effective set of parameters reduces the set-up and programming burden on clinicians. Particular embodiments take into account the patient's use of medications, the level of confidence that the device delivering the stimulation signal is properly positioned, and/or historical data that rank the likelihood of success for a variety of spinal cord locations. A general description of stimulation systems is provided below and in the context of FIG. 1. Further details of the foregoing automation methods and associated devices are discussed with reference to FIGS. 2-5B.

In other embodiments, disclosed methods and systems are directed to automatically selecting therapy programs based on efficacy of a prior program, and the location of a lead that applied the therapy. Still further embodiments are directed to selecting and testing programs in a sequential manner based on historical data, wherein the sequential distribution of the selected and tested programs is asymmetric relative to an initial location.

"High frequency" SCS systems, for example, inhibit, reduce, and/or eliminate pain via waveforms with high frequency elements or components (e.g., portions having high fundamental frequencies), generally with reduced or eliminated side effects. Such side effects can include unwanted motor stimulation or blocking, unwanted pain or discomfort, unwanted paresthesia, and/or interference with sensory functions other than the targeted pain. Accordingly, the therapy signal delivered by the system can be a non-paresthesia producing signal. In a representative embodiment, a patient may receive high frequency therapeutic signals with at least a portion of the therapy signal at a frequency of from about 1.5 kHz to about 100 kHz, or from about 1.5 kHz to about 50 kHz, or from about 3 kHz to about 20 kHz, or from about 5 kHz to about 15 kHz, or at frequencies of about 8 kHz, 9 kHz, or 10 kHz. These frequencies are significantly higher than the frequencies associated with conventional "low frequency" SCS, which are generally below 1,200 Hz, and more commonly below 100 Hz. Accordingly, stimulation at these and other representative frequencies (e.g., from about 1.5 kHz to about 100 kHz) is sometimes referred to herein as high frequency modulation.

Several embodiments described herein provide automated or semi-automated procedures for selecting high frequency SCS electrodes and/or other therapy parameters, and/or configuring the associated signal generators. Specific details of certain embodiments of the disclosure are described below with reference to methods for modulating one or more target neural populations (e.g., nerves) or sites of a patient, and associated implantable structures for providing the stimulation. Although selected embodiments are described below with reference to modulating the dorsal column, dorsal horn, dorsal root, dorsal root entry zone, and/or other particular regions of the spinal column to control pain, the stimulation may in some instances be directed to other neurological structures and/or target neural populations of the spinal cord and/or other neurological tissues. Some embodiments can have configurations, components or procedures different than those described in this section, and other embodiments may eliminate particular components or procedures. Accordingly, the disclosure may encompass other embodiments with additional elements and/or steps and may include other embodiments without several of the features or steps shown and described below with reference to FIGS. 1-5B.

While the systems and methods described herein are applicable to all paresthesia-free therapy systems, aspects of many of the following embodiments are described as simplifying the process of finding the most effective set of parameters (which may be grouped into a program) for high frequency SCS systems. Such descriptions are meant to be examples, and are not meant to be limiting. In other words, although the representative embodiments are described herein with respect to a high frequency SCS system, the methods may be applicable in at least some embodiments to certain types of low frequency SCS, as well as other therapy systems for treatment of pain or other conditions.

The techniques described below with reference to FIGS. 1-5B can provide an automatic or semi-automatic programming method that is more efficient, in terms of time, patient and/or clinician convenience, and/or cost, than existing manual programming procedures. The system can automatically determine the next program to test based on data relating to previous stimulation as well as historical probability distribution data collected for the current and/or other patients.

FIG. 1 schematically illustrates a representative patient therapy system 100 for providing relief from chronic pain and/or other conditions, arranged relative to the general anatomy of a patient's spinal column 191. The system 100 can include a signal generator 101 (e.g. a pulse generator), which may be implanted subcutaneously within a patient 190 and coupled to one or more signal delivery elements or devices 110. The signal delivery elements or devices 110 may be implanted within a patient 190, typically at or near the patient's spinal cord midline 189. The signal delivery elements 110 carry features for delivering therapy to the patient 190 after implantation. The signal generator 101 can be connected directly to the signal delivery devices 110, or it can be coupled to the signal delivery devices 110 via a signal link or lead extension 102. In a further representative embodiment, the signal delivery devices 110 can include one or more elongated lead(s) or lead body or bodies 111 (identified individually as a first lead 111a and a second lead 111b). As used herein, the terms lead and lead body include any of a number of suitable substrates and/or support members that carry devices for providing therapy signals to the patient 190. For example, the lead or leads 111 can include one or more electrodes or electrical contacts that direct electrical signals into the patient's tissue, such as to provide for patient pain relief. In other embodiments, the signal delivery elements 110 can include structures other than a lead body (e.g., a paddle) that also direct electrical signals and/or other types of signals to the patient 190.

Figure 5A:
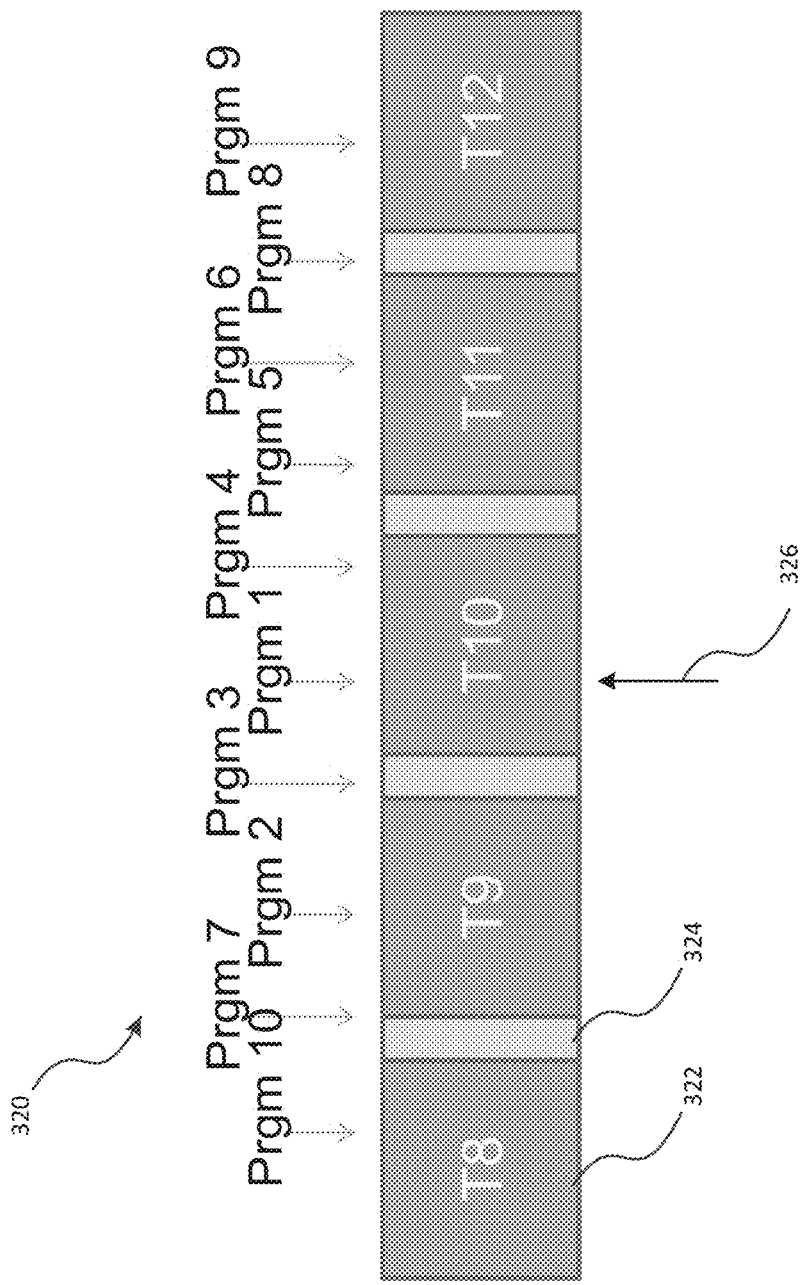
FIG. 5A illustrates a representative search algorithm for lower back pain.

In a representative embodiment, one lead 111a may be implanted on one side of the spinal cord midline 189, and a second lead 111b may be implanted on the other side of the spinal cord midline 189. The leads 111 may be positioned just off the spinal cord midline 189 (e.g., about 1 mm. offset) in opposing lateral directions so that the two leads 111 are spaced apart from each other by about 2 mm. In particular embodiments, the signal delivery devices 110 may be implanted at a vertebral level ranging from, for example, about T8 to about T12 as shown in FIG. 5A. In other embodiments, one or more signal delivery devices can be implanted at other vertebral levels, e.g., as disclosed in U.S. pending application Ser. No. 13/607,617, filed on Sep. 7, 2012, and incorporated herein by reference in its entirety.

The signal generator 101 can transmit signals (e.g., electrical signals) to the signal delivery elements 110 that up-regulate (e.g., excite) and/or down-regulate (e.g., block or suppress) target nerves. As used herein, and unless otherwise noted, the terms "modulate," "modulation," "stimulate," and "stimulation" refer generally to signals that have either type of the foregoing effects on the target nerves. The signal generator 101 can include a machine-readable (e.g., computer-readable) medium containing instructions for generating and transmitting suitable therapy signals. The signal generator 101 and/or other elements of the system 100 can include one or more processor(s) 107, memory unit(s) 108, and/or input/output device(s) 112. Accordingly, the process of providing stimulation signals, providing guidance information for positioning the signal delivery devices 110, and/or executing other associated functions can be performed by computer-executable instructions contained by computer-readable media located at the pulse generator 101 and/or other system components. The signal generator 101 can include multiple portions, elements, and/or subsystems (e.g., for directing signals in accordance with multiple signal delivery parameters), carried in a single housing, as shown in FIG. 1, or in multiple housings.

The signal generator 101 can also receive and respond to an input signal received from one or more sources. The input signals can direct or influence the manner in which the therapy instructions are selected, executed, updated and/or otherwise performed. The input signal can be received from one or more sensors 112 (one is shown schematically in FIG. 1 for purposes of illustration) that are carried by the signal generator 101 and/or distributed outside the signal generator 101 (e.g., at other patient locations) while still communicating with the signal generator 101. The sensors 112 can provide inputs that depend on or reflect patient state (e.g., patient position, patient posture and/or patient activity level), and/or inputs that are patient-independent (e.g., time). Still further details are included in co-pending U.S. application Ser. No. 12/703,683, filed on Feb. 10, 2010 and incorporated herein by reference in its entirety.

In some embodiments, the signal generator 101 can obtain power to generate the therapy signals from an external power source 103. The external power source 103 can transmit power to the implanted signal generator 101 using electromagnetic induction (e.g., RF signals). For example, the external power source 103 can include an external coil 104 that communicates with a corresponding internal coil (not shown) within the implantable signal generator 101. The external power source 103 can be portable for ease of use. In one embodiment, external power source 103 can by-pass an implanted signal generator and generate a therapy signal directly at the signal delivery device 110 (or via signal relay components).

In another embodiment, the signal generator 101 can obtain the power to generate therapy signals from an internal power source, in addition to or in lieu of the external power source 103. For example, the implanted signal generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

During at least some procedures, an external stimulator or trial modulator 105 can be coupled to the signal delivery elements 110 during an initial portion of the procedure, prior to implanting the signal generator 101. For example, a practitioner (e.g., a physician and/or a company representative) can use the trial modulator 105 to vary the stimulation parameters provided to the signal delivery elements 110 in real time, and select optimal or particularly efficacious parameters. These parameters can include the location from which the electrical signals are emitted, as well as the characteristics of the electrical signals provided to the signal delivery devices 110. In a typical process, the practitioner uses a cable assembly 120 to temporarily connect the trial modulator 105 to the signal delivery devices 110. The practitioner can test the efficacy of the signal delivery devices 110 in an initial position. The practitioner can then disconnect the cable assembly 120 (e.g., at a connector 122), reposition the signal delivery devices 110, and reapply the electrical signals. This process can be performed iteratively until the practitioner obtains the desired position for the signal delivery devices 110. Optionally, the practitioner may move the partially implanted signal delivery devices 110 without disconnecting the cable assembly 120. Furthermore, in some embodiments, the iterative process of repositioning the signal delivery devices 110 and/or varying the therapy parameters may not be performed.

The signal generator 101, the lead extension 102, the trial modulator 105 and/or the connector 122 can each include a receiving element 109. Accordingly, the receiving elements 109 can be patient implantable elements, or the receiving elements 109 can be integral with an external patient treatment element, device or component (e.g., the trial modulator 105 and/or the connector 122). The receiving elements 109 can be configured to facilitate a simple coupling and decoupling procedure between the signal delivery devices 110, the lead extension 102, the pulse generator 101, the trial modulator 105 and/or the connector 122. Receiving elements 109 can be at least generally similar in structure and function to those described in U.S. patent application Ser. No. 13/291,985, entitled MEDICAL DEVICE CONTACT ASSEMBLIES FOR USE WITH IMPLANTABLE LEADS, AND ASSOCIATED SYSTEMS AND METHODS, filed Nov. 8, 2011, which is incorporated by reference herein in its entirety.

After the signal delivery elements 110 are implanted, the patient 190 can receive therapy via signals generated by the trial modulator 105, generally for a limited period of time. During this time, the patient wears the cable assembly 120 and the trial modulator 105 outside the body. Assuming the trial therapy is effective or shows the promise of being effective, the practitioner then replaces the trial modulator 105 with the implanted signal generator 101, and programs the signal generator 101 with parameters selected based on the experience gained during the trial period. Optionally, the practitioner can also replace the signal delivery elements 110. Once the implantable signal generator 101 has been positioned within the patient 190, the signal delivery parameters provided by the signal generator 101 can still be updated remotely via a wireless physician's programmer 117 (e.g., a physician's laptop, a physician's remote, and/or another practitioner-operable device) and/or a wireless patient programmer 106 (e.g., a patient's laptop, a patient's remote, and/or another patient-operable device). Generally, the patient 190 has control over fewer parameters than does the practitioner. For example, the capability of the patient programmer 106 may be limited to starting and/or stopping the signal generator 101, and/or adjusting the signal amplitude. The patient programmer 106 may be configured to accept pain relief input as well as other variables, such as medication use.

In any of the foregoing embodiments, the parameters in accordance with which the signal generator 101 provides signals can be adjusted during portions of the therapy regimen. For example, the frequency, amplitude, pulse width and/or signal delivery location can be adjusted in accordance with a preset program, patient and/or physician inputs, and/or in a random or pseudorandom manner. Such parameter variations can be used to address a number of potential clinical situations, including changes in the patient's perception of pain, changes in the preferred target neural population, and/or patient accommodation or habituation. Certain aspects of the foregoing systems and methods may be simplified or eliminated in particular embodiments of the present disclosure. Further aspects of these and other expected beneficial results are detailed in co-pending U.S. application Ser. No. 12/765, 810, filed on Apr. 22, 2010; U.S. patent application Ser. No. 12/765,747, filed Apr. 22, 2010; and U.S. patent application Ser. No. 12/264,836, filed Nov. 4, 2008, all of which are incorporated herein by reference in their entireties.

Figure 2:
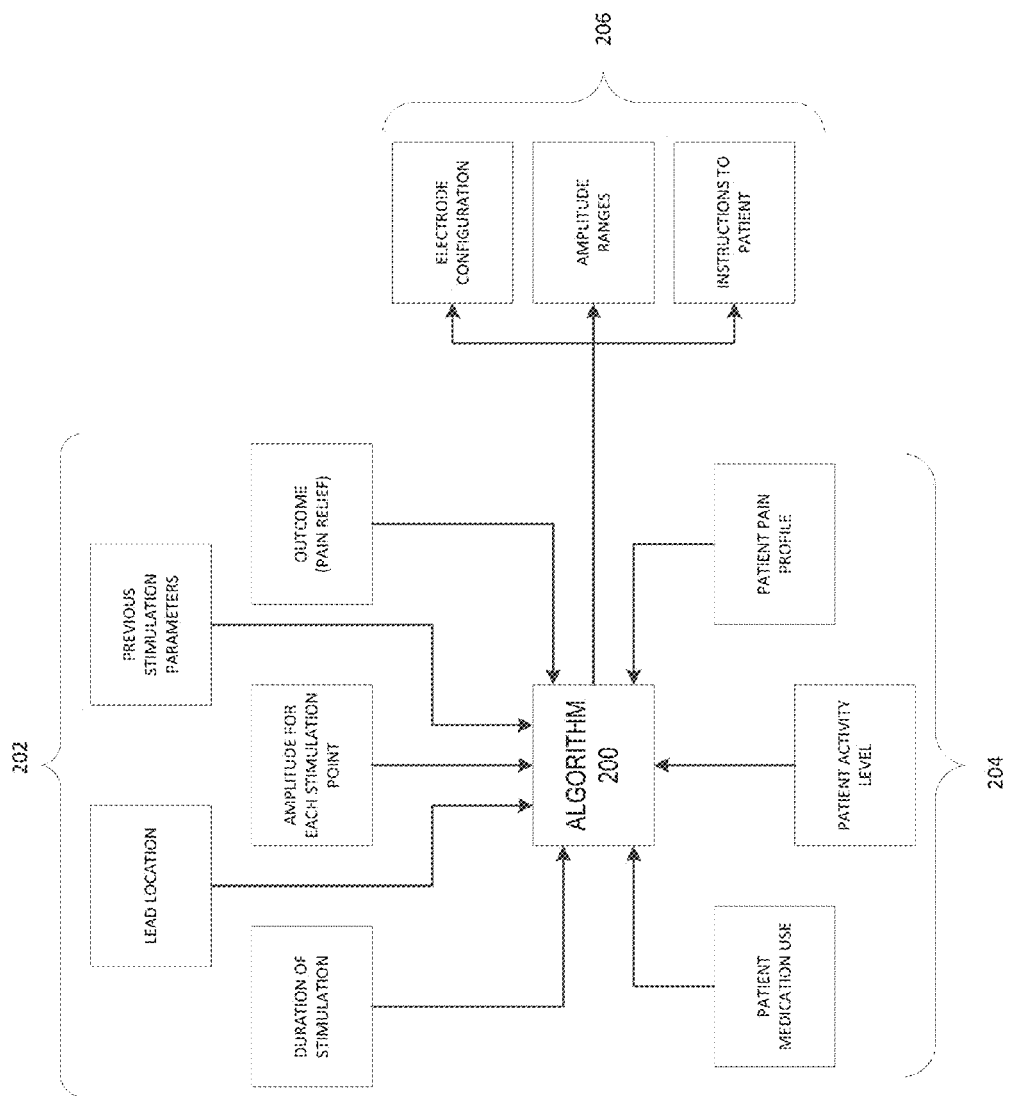
FIG. 2 is a flow diagram representation of a representative treatment algorithm and associated inputs and outputs.

As shown in FIG. 2, a representative treatment algorithm 200 operates on a plurality of required inputs 202 which include duration of the stimulation therapy, lead location (or the location of another signal delivery device), amplitude for each stimulation location, previous stimulation parameters, and outcome (e.g. pain relief). Optional inputs 204 which may be considered by the treatment algorithm 200 include patient medication use, patient activity level, and patient pain profile. The treatment algorithm 200 generates recommended output parameters 206 which include electrode configuration, amplitude ranges, and/or other therapy program parameters, and instructions to the patient and/or clinician. The algorithm 200 is included in a programmer, such as the physician's remote 117, the patient's remote 106, a trial modulator 105, or a dedicated programmer. The programmer downloads parameters and data from the signal generator 101 and uploads new programs, parameters, and/or electrode configurations to the signal generator 101.

In a particular embodiment, the clinician enters the level of pain relief provided by the system into the programmer. In another embodiment, pain relief scores are instead collected from the patient on a real time basis. This can be accomplished by having the patient enter into his/her patient remote 106 a visual analog scale (VAS) score and other inputs used by the algorithm, such as medication use or dose. The patient may be randomly prompted to provide input with an audible alarm. In another embodiment, the patient is queried for input based on the probability that there are new data available (i.e. the confidence that the current location has been suitably tested) and based on the time of day to avoid waking the patient while sleeping. The remainder of the inputs can be retrieved by the device (e.g., programmer) used to interrogate the signal generator 101 or these inputs may be used by the signal generator itself.

The signal generator keeps track of the patient's use of the given programs. This includes therapy amplitude and duration in addition to electrode configuration. When the patient is seen by the clinician, the clinician uses the programmer to interrogate the signal generator in order to retrieve this information. In addition, the programmer collects lead impedances and lead location. The programmer stores this data in a historical database that contains previous data (e.g., all previous data) retrieved for a particular patient. In a particular embodiment, the system uploads all collected data to a monitoring center that can support the patient and/or clinician. A web interface allows the patient and/or clinician to view the data and metrics indicative of the patient's progress. In a particular embodiment, an alerting service alerts the patient, clinician, physician, sales representative, or technical support of selected conditions based on the data. The foregoing information can also be collected across a patient population, and can then be used to facilitate parameter selections for individual patients, e.g., patients having the same pain indication.

The programmer places the necessary data into the treatment algorithm 200. The output parameters 206 are then uploaded to the signal generator, or a recommendation of parameters is provided to the clinician for consideration. In a particular embodiment, the clinician approves the recommended parameters and programming changes, e.g., over a web interface. The output parameters 206 may be programmed directly into the signal generator or the parameters may be communicated to the clinician who reviews and accepts the parameters, at which point the clinician can manually input the parameters into the signal generator or allow the programmer to automatically upload the parameters to the signal generator. In the case where the signal generator is programmed directly, in some instances only settings that have been previously tested in the clinic are allowed to be uploaded to the signal generator. The algorithm may also generate a set of instructions to be given to the patient outlining how to test the programs given to them.

Figure 3:
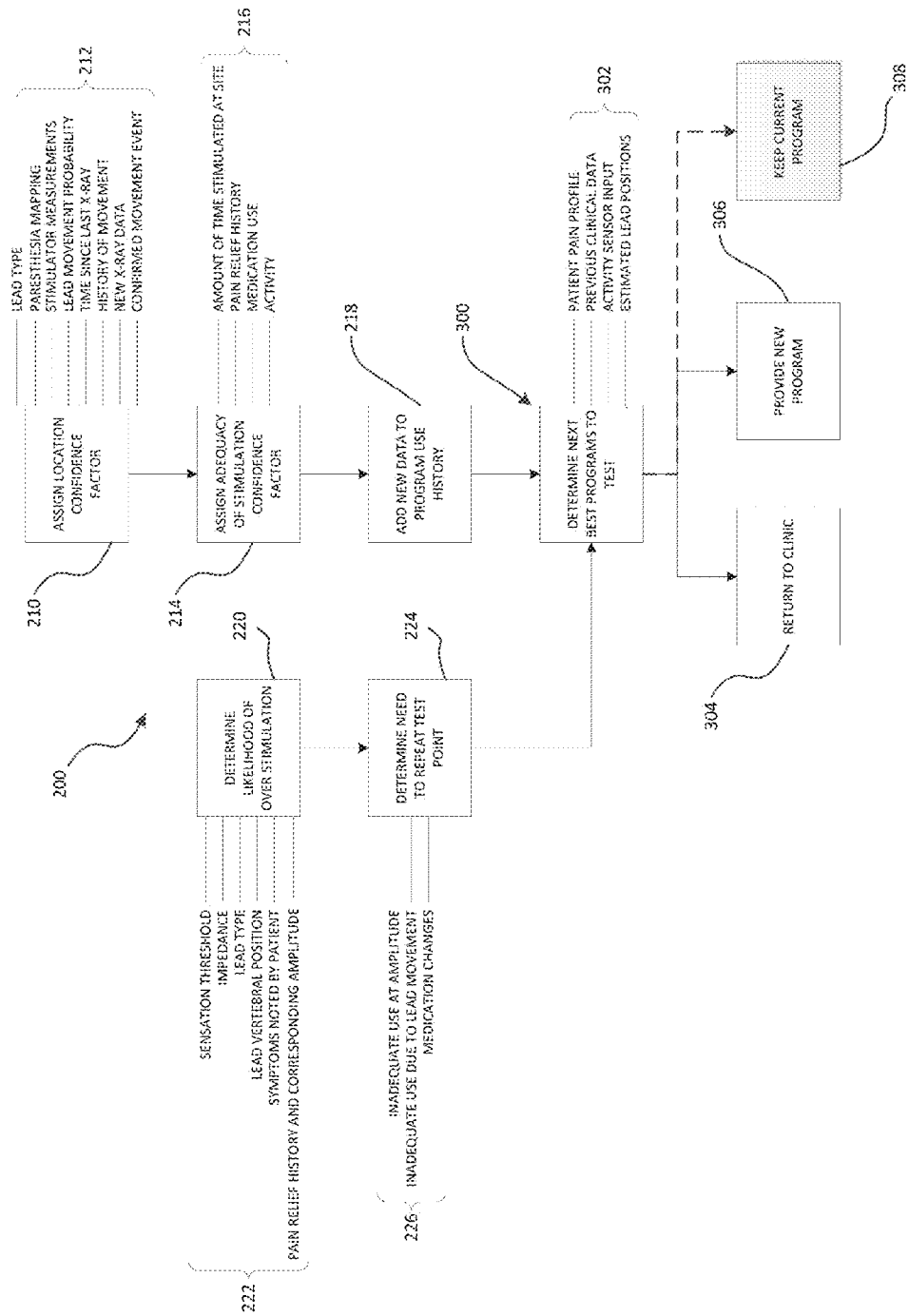
FIG. 3 is a flow diagram of a representative treatment algorithm including various modules and their associated inputs.

As shown in FIG. 3, several logic modules can make up the treatment algorithm 200. The various logic modules feed into a determination process 300 that automatically determines the next best stimulation programs to test. Module 210 assigns a location confidence factor corresponding to the degree to which the stimulation location is known. This location confidence factor can be based on location inputs 212, such as lead type used (percutaneous, paddle, etc.); paresthesia mapping; measurements (lead position, impedance, etc.) made by the modulator and/or other suitable devices; probability of lead movement (up/down and distance from clinical data); time since last x-ray/fluoro image; and the history of movement (e.g., how long the lead or other signal delivery device has been in place, and how often it has moved). The location confidence factor can be re-calculated based on new data such as a new x-ray. Also, the patient may be queried when lead movement is suspected to confirm that an event occurred that may have caused lead movement, such as a fall, lifting movement, and/or other activity. The system can alert the user that manual intervention is required if there is an indication of gross lead movement or if the location confidence factor for the lead position becomes too low (e.g., falls below a threshold level). The system may also alert the user if there is a malfunction of the device or if the leads are disconnected. In some embodiments, the programmer can automatically adjust the stimulation parameters to accommodate lead migration feedback (e.g., inputs 212). Lead movement may be determined automatically using any of a variety of suitable techniques, including those disclosed in co-pending U.S. application Ser. No. 13/645,387, filed on Oct. 4, 2012 and incorporated herein by reference in its entirety.

Module 214 assigns a confidence factor for the adequacy of stimulation at a location being tested for each amplitude used. Module 214 can base the confidence factor on stimulation inputs 216 including the amount of time a stimulation signal is applied to a particular site, pain relief history, medication use, and activity. The confidence level at a particular site typically goes up over time and then flattens out, based on clinical data. Once the confidence factors for location and stimulation adequacy are determined, they are then added to the program use history at step 218 and then fed into the determination process 300.

Modules 220 and 224 provide additional factors considered by the determination process 300. Module 220 determines the likelihood of overstimulation. This likelihood is based on overstimulation inputs 222. Overstimulation inputs 222 may include: measured sensation threshold (HF and/or LF); impedance; lead type used (paddle vs. percutaneous); lead vertebral position (cervical vs. thoracic); symptoms noted by the patient; and pain relief history along with corresponding amplitudes. Module 224 determines whether it is necessary to repeat a test point and bases this determination on repeat inputs 226. Repeat inputs 226 may include: whether there was inadequate use of a program at a given amplitude; inadequate use of the program due to lead movement; and/or whether there was interference with the test due to medication changes and/or physical activity changes.

Once the inputs from the various modules 210, 214, 220, and 224 are fed into the determination process 300, the process 300 outputs a new program 306, outputs instructions for the patient to return to the clinic at 304, or outputs the current program at 308. Determination process 300 may also consider one or more additional factors 302 which include patient pain profile, previous clinical data, input from an activity sensor, and estimated lead positions.

TABLE 1

|  | Monday | Tuesday | Wednesday | Thursday |
| --- | --- | --- | --- | --- |
| Program | 1 | 2 | 2 | 3 |
| Medication | YES | YES | YES | NO |
| Pain Relief | YES | YES | YES | NO |

Table 1 illustrates a representative scenario of a patient's use of a spinal cord stimulation system and the associated parameters over a course of several days. As shown in Table 1, data for each day may include the program used, whether medication was used, and the level of pain relief resulting from the program and medication. It should be appreciated that Table 1 is a simplified representation of the retrieved data. For example, the level of pain relief may be more detailed, such as a VAS score (or another suitable measure). Similarly, the level of medication use may be indicated by a dosage level, for example. Furthermore, it should be understood that the level of medication and level of pain relief may be input into the signal generator by the patient, via a patient remote, on a daily basis or other time increment. In addition, although Table 1 is shown with time increments of days, other time increments can be used, such as, for example, hours or minutes. Given the data, such as in Table 1, the treatment algorithm analyzes the data in order to search for ineffective days to determine if particular programs (e.g., parameters or combinations of parameters) should be repeated.

Figure 4:
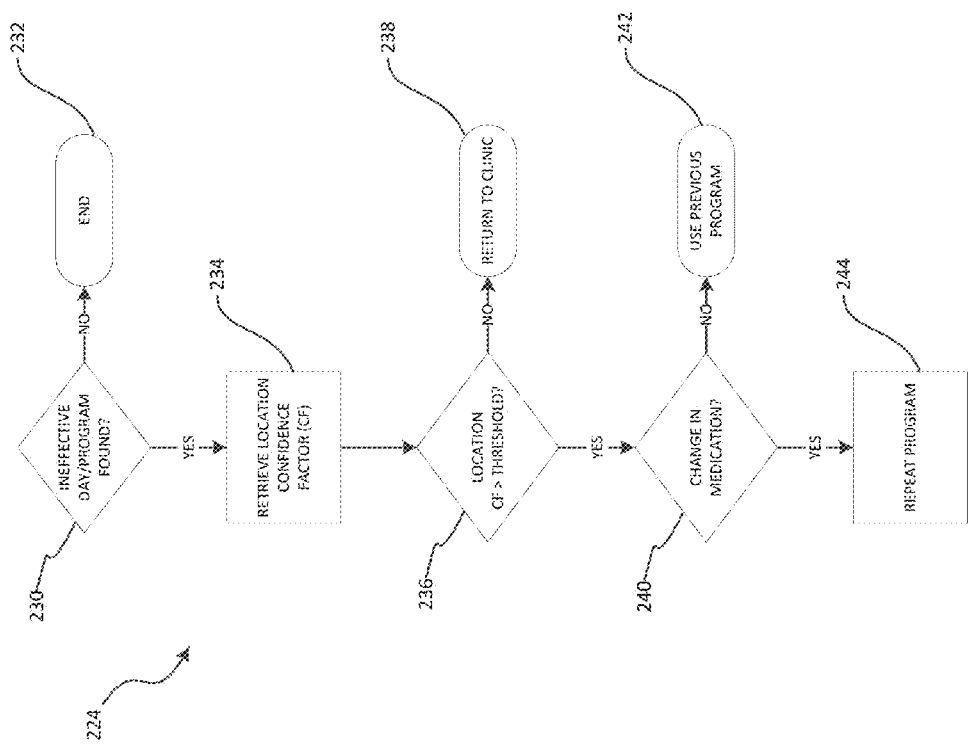
FIG. 4 is a detailed flow diagram illustrating the logic of a representative module for determining the necessity of repeating a program.

FIG. 4 illustrates in further detail the logic for module 224 used to determine whether a program should be repeated. At step 230 the data are interrogated to determine if any of the days were ineffective (or below a threshold effectiveness level). For example, the therapy for Thursday is indicated as being ineffective—pain relief is listed as (NO). Accordingly, Thursday can represent a target time period having a corresponding level of efficacy (that in this case is very low or zero). In the case when no days having relatively low effectiveness are found, the process ends at step 232. However, when a day having sub-threshold effectiveness level is found, as in this example, the process moves to step 234 where the location confidence factor is retrieved. This part of the process seeks to eliminate other variables which may cause the treatment to be below an effectiveness threshold. In this case, if the lead location has moved, that movement may be responsible for the low efficacy and the patient can be instructed at step 236 to return to the clinic at step 238 to have the lead repositioned or remapped. For example, at step 236 if the location confidence factor is below a practitioner-selected threshold, the patient is instructed at step 238 to return to the clinic. However, in the case for which the location confidence factor is greater than the threshold, the process continues to step 240 where it is determined whether the patient's medication has changed, which could affect the efficacy of the program in question. Again, with reference to Table 1, the patient was taking medication on Wednesday (the immediately preceding or prior time period, as indicated by the response YES) but was not taking medication on Thursday (NO). Thus, the patient's medication changed at the same time that Program 3 was indicated as ineffective. Therefore, in this example, the patient's medication changed (i.e., the patient stopped taking medication) which may account for Program 3 being ineffective on Thursday. Thus, moving to step 244, Program 3 will be repeated. In the case for which there was no change in the patient's medication, the previous program (Program 2) can be repeated to provide pain relief and Program 3 may be categorized as ineffective and stored in the database history as such.

FIG. 5A illustrates another embodiment of a therapy algorithm in the form of a search algorithm 320 that includes Programs 1-10, which may be used to treat lower back pain, for example. As shown schematically in the Figure, the vertebral bodies 322 are separated by disks 324. In this example, vertebral bodies T8 through T12 are illustrated. In a particular embodiment, Programs 1-10 are activated in numerical sequence at the axial locations shown. The sequence can be determined empirically from historical data. In some embodiments, the lead can be positioned asymmetrically with respect to the expected target for pain relief along the patient's spine (e.g. the "sweet spot"). This arrangement can be used when the historical data indicate more likely candidate sites on one side (axially) of the target location than on the opposite side. For example, as shown in FIG. 5A, the lead is positioned with five candidate lead locations caudal (i.e., toward the tail bone) of an initial vertebral target location 326 and four candidate locations cephalic (i.e., toward the head). In the clinic and/or during a trial period, many or all of the expected locations/amplitudes to be used can be tested for sensation thresholds and patient tolerance. This can be done with an automated system that is directed by the patient, where the patient holds a button to let the test proceed and then releases the button if they feel any sensation (stopping the test for that location). The test cycles through the amplitudes/frequency/pulse width as needed for each location.

Figure 5B:
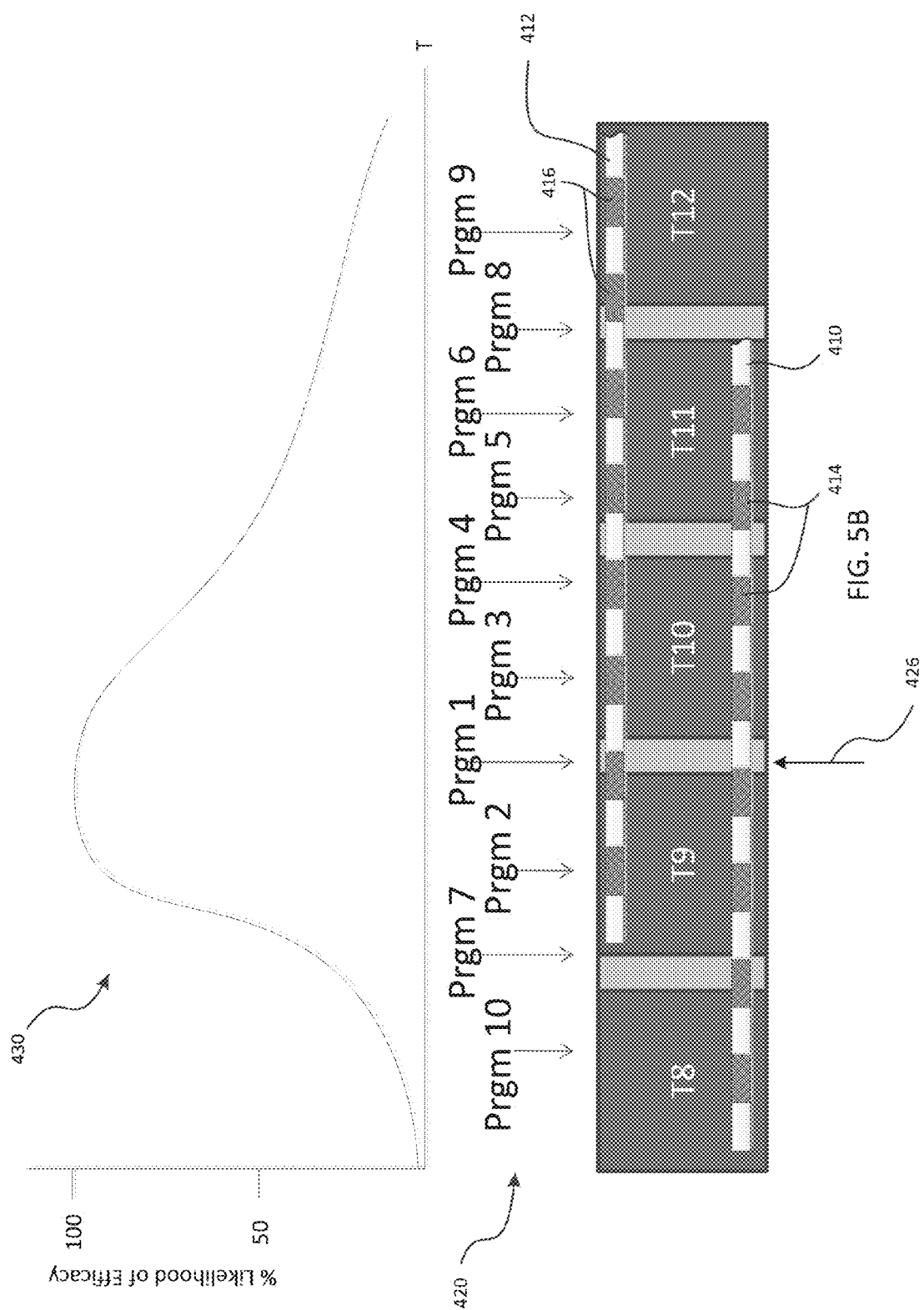
FIG. 5B illustrates another representative search algorithm for lower back pain.

FIG. 5B illustrates a particular representative embodiment of a set of therapy programs 420 (e.g., Programs 1-10) asymmetrically distributed about an initial vertebral target location 426. In this embodiment, Programs 1-10 are distributed along the spine based on a probability curve 430. Probability curve 430 represents an empirically derived likelihood of effective therapy (e.g., pain relief) as a function of vertebral location (T). In this embodiment, Programs 1-10 are distributed with a majority of the programs caudal of the initial vertebral target location 426. Each Program 1-10 represents a set of stimulation parameters, including which contacts are activated. Typically, two contacts are activated on a single signal delivery device to form a bipolar pair. In other embodiments, a program can include more or fewer contacts, and/or the contacts in a given program can span multiple leads.

Each signal delivery device 410 and 412 can include a plurality of contacts 414 and 416, respectively. As shown in FIG. 5B, a majority of the plurality of contacts are located caudal of the initial vertebral target location 426, in accordance with the probability curve 430. While the above embodiments are described as having an asymmetric distribution of therapy programs and contacts biased in a caudal direction with respect to a target location, in some embodiments the programs and contacts can have an asymmetric distribution biased in a cephalic direction.

A representative method for treating a patient in accordance with an embodiment of the present disclosure, as reflected in FIG. 5B, includes receiving an indication of a first location (e.g., the initial vertebral target location 426) at which a stimulation signal has been applied to the patient's spinal cord via an implanted signal delivery device (e.g., a lead). The method can further include receiving historical data corresponding to the efficacy of a plurality of candidate locations (e.g., locations indicated by Programs 2-10). Based at least in part on the historical data, the method can further include sequentially selecting and testing at least some of the candidate locations, wherein a sequential distribution of the selected and tested candidate locations is asymmetric relative to the first location. The process of selecting and testing at least some of the candidate locations can be triggered by an indication that the efficacy at the first location is below a target level.

An associated spinal cord stimulation system can include a signal generator coupleable to an implantable signal delivery device (e.g., a lead), a trial modulator, also coupleable to the implantable signal delivery device, and an external device programmed with instructions for directing the signal generator. The external device can include a patient-operable device or a practitioner-operable device, for example. The signal generator, the trial modulator and/or the external device include instructions that when executed, receive an indication of a first location at which a stimulation signal has been applied by the signal generator to the patient's spinal cord via the implantable signal delivery device. The instructions further receive historical data corresponding to the efficacy of a plurality of candidate locations and, based at least in part on the historical data, sequentially select and test at least some of the candidate locations. As discussed above, the sequential distribution of the selected and tested candidate locations can be asymmetric relative to the first location.

An advantage of the foregoing arrangement is that it can make use of historical data to select new programs in a manner that may be non-intuitive, and that may reduce the amount of time required to select a program that meets efficacy thresholds, in cases for which the first selected program does not. In particular, many conventional routines for selecting a suitable program include centering the lead or other stimulation device at the target site and delivering a signal via the electrode or electrodes closest to that site. If those electrodes do not produce suitable results, the electrodes are sequentially tested in a manner that simply works outwardly from the central electrode. Accordingly, the adjacent cephalic electrode can be tested first and if it is not effective, the electrode located immediately caudal to the first electrode is tested. If that caudal electrode is not successful, the sequence includes going to the next closest cephalic electrode, then the next closest caudal electrode, etc. until all of the electrodes are tested. Such an arrangement fails to account for the fact that the ranking of effective target locations may not simply oscillate back and forth on alternate sides of the central-most location at which the lead is placed. Instead, as shown in FIG. 5B, the locations can have an asymmetric distribution about an initial target site.

Certain of the foregoing embodiments can produce one or more of a variety of advantages, for the patient and/or the practitioner, when compared with standard programming procedures. Some of these benefits were described above. For example, aspects of many of the representative embodiments disclosed herein are directed to simplifying the process of finding a better (e.g., the most effective) set of parameters or program for a high frequency stimulation system for a particular patient. As such, it is expected that the techniques described herein can provide an automatic or semi-automatic programming method that is more efficient, in terms of time and/or cost, than existing manual programming procedures. In particular embodiments, the methods track variables that may affect efficacy, e.g., medication usage and/or lead location. In other embodiments, as described above, the methods make use of historical data to select program parameters in ways that would otherwise not be intuitive.

Disclosed herein are methods for automatically programming a signal generator in a patient therapy system, such as a spinal cord stimulation system. In an embodiment, the method comprises stimulating a first electrode configuration according to a first program; receiving information from a patient regarding a level of efficacy for the first electrode configuration; receiving information regarding lead location; selecting a second program based on the level of efficacy and lead location; and stimulating a second electrode configuration according to the second program.

In one aspect of the technology disclosed herein, a confidence factor is assigned regarding lead location. In another aspect of the disclosed technology, the method may further comprise retrieving information from the signal generator regarding the first program and selecting the second program based on the information from the signal generator regarding the first program. In a further aspect of the disclosed technology, the first and second programs each include duration of stimulation and amplitude of stimulation.

Also disclosed herein is a spinal cord stimulation system. In a representative embodiment the system comprises a signal generator implantable in a patient with a first program loaded into the signal generator. The signal generator is operable to stimulate a first electrode configuration according to the first program. The system includes a patient remote that is operable to receive information from the patient regarding a level of efficacy for the first electrode configuration. The system also includes a practitioner remote that is operable to retrieve the level of efficacy for the first electrode configuration, operable to receive information regarding lead location, and operable to automatically select a second program based on the level of efficacy and lead location. The signal generator being operable to stimulate a second electrode configuration according to the second program.

In other aspects of the disclosed technology, the system further comprises at least one memory unit operable to record the information from the patient. The at least one memory unit may be housed in the signal generator. In another aspect of the disclosed technology, the patient remote is operable to communicate with the signal generator.

In a particular embodiment, any one or more of the above-described paresthesia-free modulation therapies may be applied at specific duty cycles that have shown superior results over large population pools. For example, the therapy signal can be applied at duties cycle wherein the modulation is on for a period of from about 1 msec. to about 2 seconds, and off for a period of from about 1 msec. to about 1.5 seconds. In other embodiments, longer on and off time periods have also produced superior results. For example, in a representative embodiment, the high frequency modulation signal can be on for approximately 20 seconds and off for approximately 120 seconds. In another embodiment, the high frequency modulation signal can be on for 10-20 seconds and off for 60-120 seconds. In a particular embodiment, the stimulation may be applied generally at a duty cycle of around 10%.

In certain embodiments, the amplitude of the therapy signal can range from about 0.1 mA to about 20 mA, or from about 0.5 mA to about 10 mA, or from about 0.5 mA to about 4 mA, or from about 0.5 mA to about 2.5 mA. The amplitude of the applied signal can be ramped up and/or down. In particular embodiments, the amplitude can be increased or set at an initial level to establish a therapeutic effect, and then reduced to a lower level to save power without forsaking efficacy, as is disclosed in pending U.S. application Ser. No. 12/264,836, incorporated herein by reference in its entirety.

In certain embodiments, the pulse width (e.g., for just the cathodic phase of the pulses) can vary from about 10 microseconds to about 333 microseconds. In further particular embodiments, the pulse width can range from about 25 microseconds to about 166 microseconds, or from about 33 microseconds to about 100 microseconds, or from about 50 microseconds to about 166 microseconds.

In some embodiments, applying a short pulse width waveform via the signal generator and the signal delivery device is effective in providing pain relief without generating paresthesia. Many such examples are described herein in the context of high frequency signals (e.g., signals with a frequency of 1.5 kHz to 100 kHz). In other embodiments, the signals can have short pulse widths, at high or low frequencies. In particular examples, the signal (or at least a portion of the signal) can have pulses with pulse widths ranging from about 10-50 microseconds, or from about 20-40 microseconds, or from about 25-35 microseconds, or from about 30-35 microseconds, or about 30 microseconds. The amplitude of the waveform (e.g., the amplitudes of the individual pulses) can be from about 0.5-20 mA, or from about 2-18 mA, or from about 5-15 mA, or from about 7-10 mA, or about 0.5-7 mA. Meanwhile, the frequency of the therapy signal (or at least a portion of the signal) can be at or below 1.5 kHz, e.g., from about 2 Hz to about 1.5 kHz, or from about 500 Hz to about 1.5 kHz, or from about 700 Hz to about 1.5 kHz, or from about 1 kHz to about 1.5 kHz, or about 1.2 kHz. In one representative example, the therapy signal includes a frequency of 1,200 Hz, a pulse width of 30 microseconds, and an amplitude that provides pain relief without generating paresthesia (generally between 0.5-20 mA).

In any of the foregoing embodiments, aspects of the therapy provided to the patient may be varied within or outside the representative parameters described above, while still obtaining beneficial results for patients suffering from chronic pain and/or other indications. For example, the location of the signal delivery device (and in particular, the signal delivery device electrical contacts or electrodes) can be varied over the significant lateral and/or axial ranges.

The specific values selected for the foregoing parameters may vary from patient to patient and/or from indication to indication and/or on the basis of the selected vertebral location. In addition, the methodology may make use of other parameters, in addition to or in lieu of those described above, to monitor and/or control patient therapy. For example, in particular embodiments, the signal amplitude refers to the electrical current level, e.g., for current-controlled systems. In other embodiments, the signal amplitude can refer to the electrical voltage level, e.g., for voltage-controlled systems. In cases for which the signal generator includes a constant voltage arrangement rather than a constant current arrangement, the current values described above may be replaced with corresponding voltage values.

Many embodiments of the technology described above may take the form of computer-executable instructions, including routines executed by a programmable computer. Those skilled in the relevant art will appreciate that the technology can be practiced on computer systems other than those shown and described below. The technology can be embodied in a special-purpose computer or data processor that is specifically programmed, configured or constructed to perform one or more of the computer-executable instructions described below. Accordingly, the term "computer" or "controller" as generally used herein refers to any suitable data processor and can include Internet appliances and hand-held devices (including palm-top computers, wearable computers, cellular or mobile phones, multi-processor systems, processor-based or programmable consumer electronics, network computers, mini computers and the like). Information handled by these computers can be presented at any suitable display medium, including a CRT display or LCD.

The technology can also be practiced in distributed environments, where tasks or modules are performed by remote processing devices that are linked through a communications network. In a distributed computing environment, program modules or subroutines may be located in local and remote memory storage devices. Aspects of the technology described below may be stored or distributed on computer-readable media, including magnetic or optically readable or removable computer disks, as well as distributed electronically over networks. In particular embodiments, data structures and transmissions of data particular to aspects of the technology are also encompassed within the scope of the technology.

From the foregoing, it will be appreciated that specific embodiments of the disclosed technology have been described herein for purposes of illustration, but that various modifications may be made without deviating from the technology. For example, computer program steps or processes described in the context of one system component (e.g., a physician programmer) can in at least some embodiments be carried out by another system component or components (e.g., an implanted signal generator or external stimulator). Certain aspects of the disclosure described in the context of particular embodiments may be combined or eliminated in other embodiments. Therapies directed to particular indications may be combined in still further embodiments. Additional indicators are disclosed in pending U.S. application Ser. No. 13/607,617, previously incorporated herein by reference. Further, while advantages associated with certain embodiments have been described in the context of those embodiments, other embodiments may also exhibit such advantages, and not all embodiments need necessarily exhibit such advantages to fall within the scope of the present disclosure. Accordingly, the present disclosure and associated technology can encompass other embodiments not expressly shown or described herein.

We claim:
1. A spinal cord stimulation system, comprising:
   a signal generator implantable in a patient and programmed with instructions that, when executed, direct the signal generator to apply a therapy signal to the patient via a signal delivery device according to a first program;

a patient-operable device programmed with instructions that, when executed, receive information from the patient regarding a level of efficacy for the first program;

at least one memory unit housed in the signal generator and operable to record the information from the patient;

a practitioner-operable device programmed with instructions for directing the signal generator;

wherein at least one of the signal generator and the practitioner-operable device is programmed with instructions that, when executed:

retrieve the level of efficacy for the first program from the at least one memory unit, receive information corresponding to a location of the signal delivery device, and automatically select a second program based on the level of efficacy and signal delivery device location; and wherein the signal generator is programmed with instructions, that when executed, direct the signal generator to apply a therapy signal to the patient according to the second program.

2. The system of claim 1 wherein at least one of the signal generator and the practitioner-operable device is programed with instructions that, when executed, assign a confidence factor to the signal delivery device location, and wherein automatically selecting the second program is performed only when the confidence factor exceeds a threshold value.

3. The system of claim 1 wherein at least one of the signal generator and the practitioner-operable device is programed with instructions that, when executed, retrieve information from the signal generator regarding the first program, and wherein selecting the second program is based on the information from the signal generator regarding the firstprogram.

4. The system of claim 1 wherein at least one of the signal generator and the practitioner-operable device is programed with instructions that, when executed, receive information corresponding to the patient's medication use, and wherein selecting the second program based at least in part on the information corresponding to the patient's medication use.

5. The system of claim 1, wherein the patient operable device is operable to communicate with the signal generator.

6. The system of claim 1, wherein the level of efficacy corresponds to a level of pain relief.

7. The system of claim 1, wherein information regarding lead location is obtained from an x-ray of the patient.

8. The system of claim 1, wherein the first and second programs each include information pertaining to duration of stimulation and amplitude of stimulation.

9. The system of claim 1, wherein the first program includes a first electrode configuration and the second program includes a second electrode configuration different than the first electrode configuration.

10. The system of claim 1, wherein the therapy signal according to at least one of the first and second programs has a frequency in a range of from about 1.5 kHz to about 100 kHz.

11. The system of claim 1, wherein the signal generator is programmed with instructions that, when executed, direct a non-paresthesia producing signal having a frequency in a range of from about 1.5 kHz to about 100 kHz to the patient.

* * * * *